United States Patent [19]
Platsch

[11] Patent Number: 6,115,490
[45] Date of Patent: Sep. 5, 2000

[54] APPARATUS FOR DETERMINING THE POWDER DENSITY ON A DUSTY PRINTED ARTICLE

[76] Inventor: Hans Platsch, Kupferstr. 40, D-70565 Stuttgart, Germany

[21] Appl. No.: 08/952,532

[22] PCT Filed: Apr. 22, 1996

[86] PCT No.: PCT/EP96/01680

§ 371 Date: Dec. 29, 1997

§ 102(e) Date: Dec. 29, 1997

[87] PCT Pub. No.: WO96/35939

PCT Pub. Date: Nov. 14, 1996

[30] Foreign Application Priority Data

May 7, 1995 [DE] Germany ............................ 195 16 188

[51] Int. Cl.[7] .................................................. G06K 9/00
[52] U.S. Cl. .......................... 382/141; 382/108; 382/144; 382/192; 382/321; 250/559.46; 356/225; 356/237; 348/128
[58] Field of Search .................................... 382/108, 112, 382/144, 145, 149, 192; 250/559.46, 564; 356/138, 218, 225, 237, 338, 339, 340, 375, 376, 400, 431, 141.3, 141.2, 141.4; 348/86, 125, 128

[56] References Cited

U.S. PATENT DOCUMENTS

| | | | |
|---|---|---|---|
| 4,568,188 | 2/1986 | Weber | 356/225 |
| 4,660,980 | 4/1987 | Takabayashi et al. | 356/345 |
| 4,974,261 | 11/1990 | Nakahara et al. | 382/192 |
| 5,274,713 | 12/1993 | Chang et al. | 250/559.46 |
| 5,301,244 | 4/1994 | Parulski | 382/59 |
| 5,317,380 | 5/1994 | Allemand | 356/338 |
| 5,608,817 | 3/1997 | Yamaoka et al. | 382/141 |
| 5,680,473 | 10/1997 | Kanzaka et al. | 348/128 |
| 5,715,052 | 2/1998 | Fujino et al. | 356/237 |
| 5,907,405 | 5/1999 | Mizutani et al. | 356/399 |

*Primary Examiner*—Matthew Bella
*Assistant Examiner*—Sheela Chawan

[57] ABSTRACT

To generate a high-contrast image of powder particles located on the surface of a print product, a measurement apparatus has an illumination unit which generates a measurement light beam which strikes the surface of the print product at glancing incidence. A measurement optics has an axis vertical to the surface of the print product and a diaphragm body is arranged in its focal point on the image side. The measurement optics forms an image of a surface region of the dusted print product on an image converter. An electronic evaluation unit determines the number and size of the powder particles from the image obtained on the image converter.

26 Claims, 6 Drawing Sheets

APPARATUS FOR DETERMINING THE POWDER DENSITY ON A DUSTY PRINTED ARTICLE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention relates to an apparatus for determining the powder density on a dusted print product according to the preamble of claim 1.

2. Discussion of the Relevant Art

The prior patent application 195 01 346.8 relates to a measurement apparatus of this kind.

SUMMARY OF THE INVENTION

The invention is intended to develop a measurement apparatus of this kind in such a way that a further improved identification of the individual powder particles located on the printed print product is guaranteed.

For a corresponding contrast intensification, according to the distinguishing feature of claim 1 it is proposed to arrange a diaphragm body at the image-side focal point of the optics forming an image of a region of the surface of the print product on the image converter. As the axis of the optics is set at an angle to the surface of the print product which is different from the angle of reflection of the measurement light beam, a further improved suppression of light not reflected by powder particles is obtained in this way.

Advantageous developments of the invention are quoted in sub-claims.

In the items of measurement apparatus according to claim 2 and 3 the form of the opening provided in the diaphragm body is matched to the geometry of the particular image converter used.

With a measurement apparatus according to claim 4, the print product may be reliably measured in a simple manner.

With the development according to claim 5 it is possible reliably to extend the powder density measurement to the entire region of the print product, and thus not only measure in one direction, which runs transverse to the direction in which the print product is fed through the dusting apparatus, but also in the feed direction itself. In this way it is possible not only to determine whether some of the nozzles of the powder dusting apparatus, which are arranged crosswise to the feed direction of the print product, are dispensing uneven quantities of powder, but also to determine whether the different powder dispensing nozzles are operating constantly, i.e. without variations in time.

The development of the invention according to claim 6 enables a measurement apparatus to be produced on the basis of basic components which are obtainable on the market at low cost, and which need only slight modification.

The development of the invention according to claim 7 is advantageous in respect of a further improvement of the contrast when representing the powder particles.

The development of the invention according to claim 8 permits a glancing illumination of the surface of the print product with compact dimensions of measurement head and illumination unit.

The purpose of the development of the invention according to claim 9 is also to increase the contrast when generating the powder particle image, as reflections of measurement light on the underside of the housings of measurement head and illumination unit are eliminated.

According to claim 10, a common commercial scanner can be converted into a powder density measurement apparatus with simple means and without major intervention in the scanner.

With the development of the invention according to claim 11 it is achieved that the entrance window of the scanner is raised somewhat from the surface of the print product so that the powder particle distribution is not changed when the scanner is moved. At the same time, a small slit-shaped chamber, via which the measurement light beam is supplied, is created between the underside of the scanner housing and the surface of the print product.

With the development of the invention according to claim 12, an electronic contrast increase for the production of the image of the powder particles located on the surface of the print product is obtained at the same time by simple means.

The same advantage is obtained according to claim 13 for the representation of surface roughnesses on a print support.

The development of the invention according to claim 14 permits the same software to be used for determining the surface roughnesses as regards number and size as for determining the powder density and the size of the various powder particles.

The developments of the invention according to claims 15 to 17 are advantageous in respect of particularly simple determination of the number and size of objects (powder particles and/or roughnesses) found on the surface of the print product and/or the print support.

With a measurement apparatus according to claim 18 and 19, a notification of the operator is automatically obtained if the powder density either drops so low that a reliable separation of superimposed print products is no longer assured or if it rises locally to such an extent that contamination of the printing machine by excess powder is to be feared.

With a measurement apparatus according to claim 20, after measuring the surface roughness of a print support the user obtains a suggestion as to which type of powder is to be used in what quantity for the reliable separation of superimposed printed print sheets.

With a measurement apparatus according to claim 21, the angle of incidence of the measurement light beam can be varied, and the conditions which are most favourable in each case for the measurement of the powder density and the measurement of the surface roughnesses can thus be set. To measure the powder density, as glancing an incidence of the measurement light beam as possible is of advantage, whereas when determining the number and dimensions of surface roughnesses a slightly stronger setting of the axis of the measurement light beam is advantageous.

BRIEF DESCRIPTION OF THE DRAWINGS

The invention will be explained in greater detail below with the aid of embodiments, with reference to the drawings in which.

DETAILED DESCRIPTION OF PREFERRED EMBODIMENTS

Figure 1:
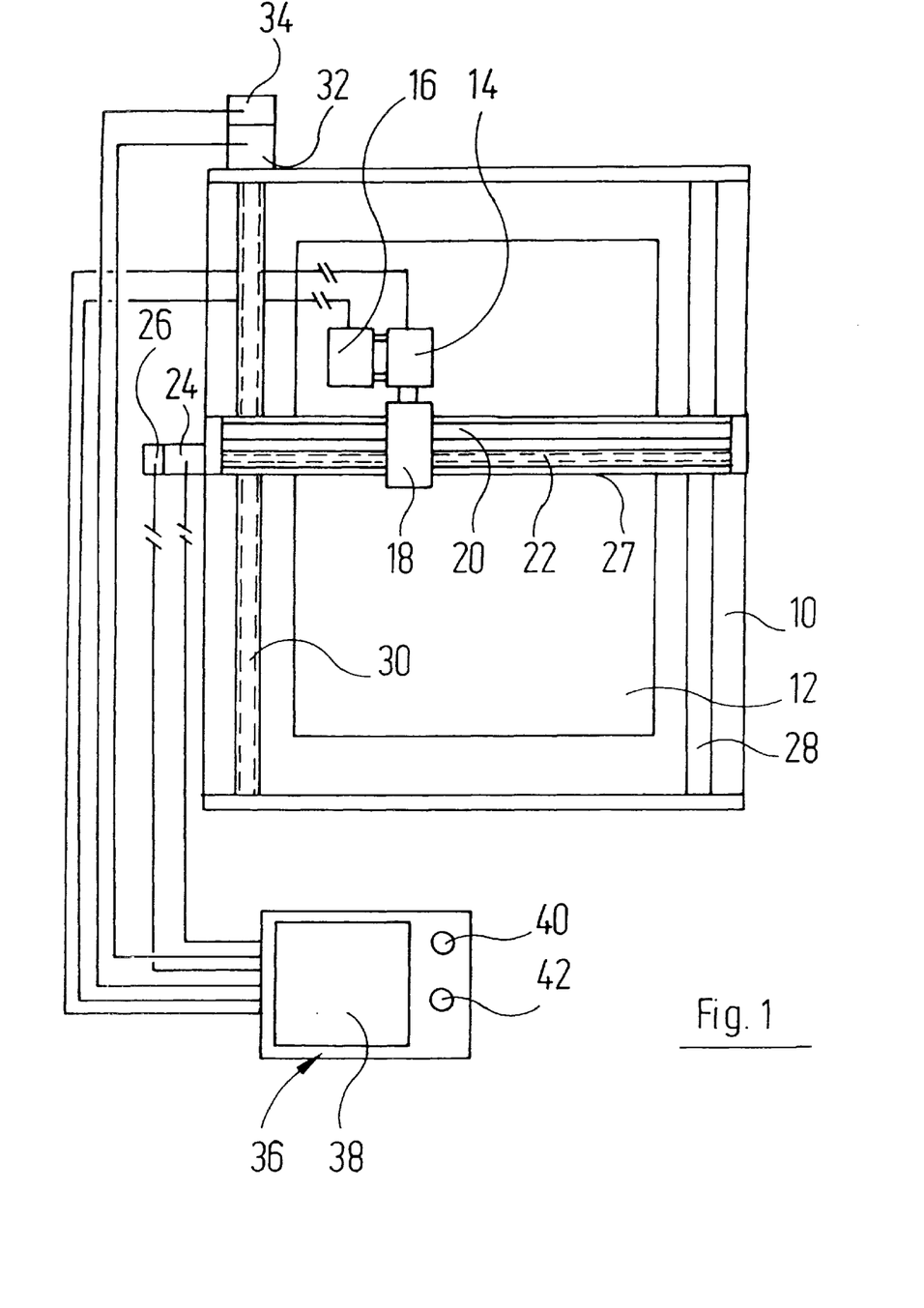
FIG. 1 shows a schematic top view of a measurement apparatus for determining the powder density on a printed print product and for determining the surface roughness of a print support to be printed.

In FIG. 1, 10 denotes a measurement table on which a sheet-shaped printed print product 12 lies. After printing this has been dusted with a thin layer of powder which prevents print products in a stack from sticking together. An optical measurement head, which is denoted overall by 14 and which for its part carries an illumination unit 16, is provided above the print product so as to be able to measure whether the powder density is adequate overall but not, on the other hand, unnecessarily high.

The measurement head 14 is fixed to a slide 18 which runs on a guide rod 20 and is driven by a threaded spindle 22. The latter is rotated by a motor 24 which is coupled to a synchro generator 26.

For its part a slide 27 bearing the guide rod 20 and the threaded spindle 22 runs on a guide rod 28 and is moved by a threaded spindle 30 which is driven by a motor 32. A synchro generator 34 is assigned to the latter.

A control and evaluation unit denoted overall by 36 is used to evaluate the part-images of the surface of the print product 12 generated by an image converter of the measurement head 14 as well as to supply energy to the illumination unit 16 and to control the motors 24 and 32 and to measure the position of the two slides 18 and 27. In the lines extending between the control and evaluation unit 36 and the connected units, line sections which are flexible and/or of variable length are indicated by interruptions.

Via the motors 24 and 32 the control and evaluation unit 36 moves the unit formed by the measurement head 14 and the illumination unit stepwise over the print master, the step sizes in horizontal and/or vertical direction being predetermined by the edge lengths of the image field of the measurement head 14. The control and evaluation unit 36 also evaluates the output signals of an image converter of the measurement head 14, as will be described in greater detail below.

The control and evaluation unit 36 has a display 38 which may be formed by an LCD field, for example. Operating knobs 40, 42 serve to select basic modes of operation of the control and evaluation unit 36, particularly to change over from the above-mentioned measurement of the density of powder particles to a mode of operation in which the roughness of an unprinted print support is determined.

Figure 2:
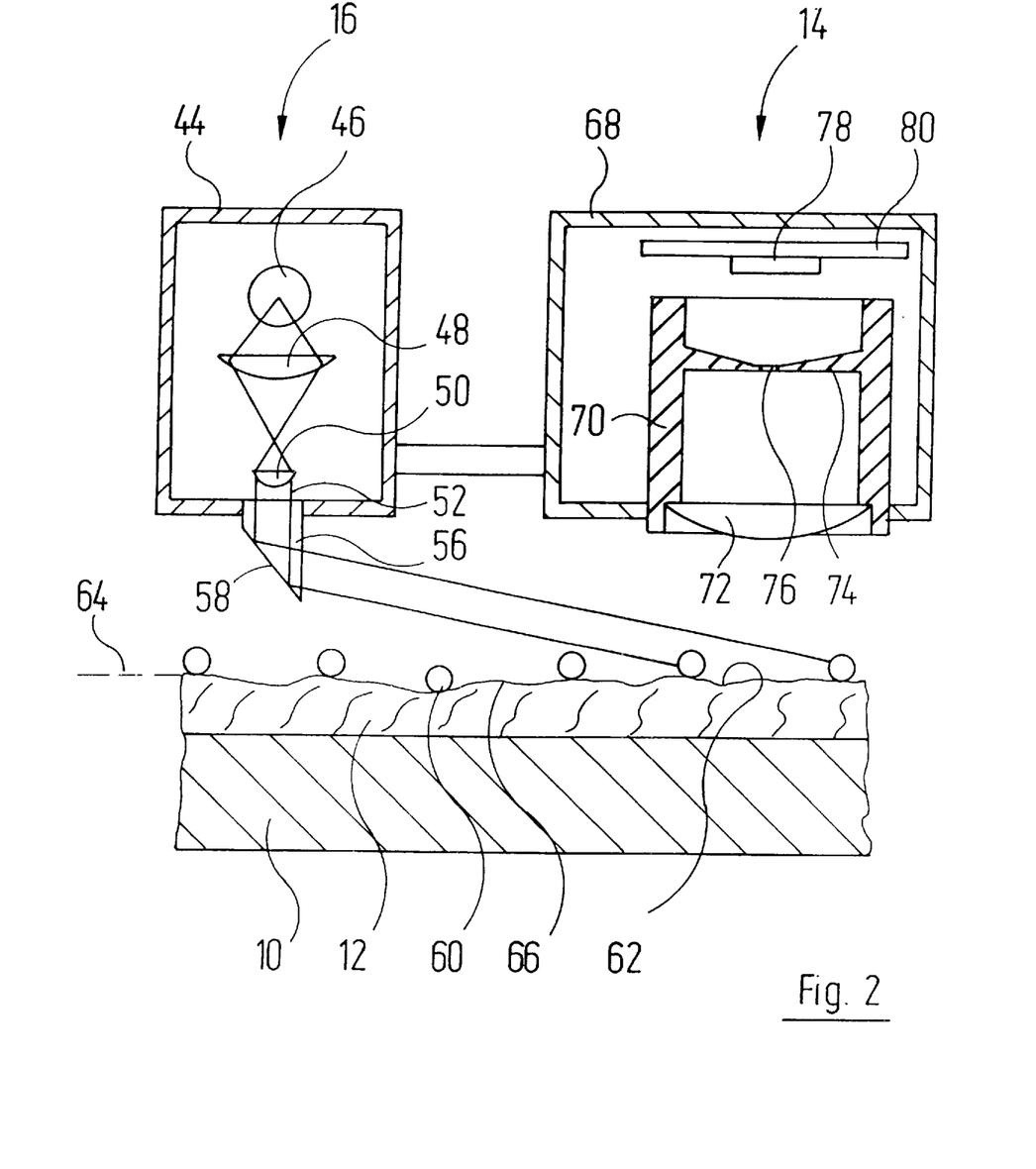
FIG. 2 shows a vertical central section through an illumination unit and a measurement head of the measurement apparatus shown in FIG. 1 and through the sections underneath of a dusted print product and a master table of the measurement apparatus of FIG. 1.

As can be seen from FIG. 2, the illumination unit 16 has a housing 44 in which a light source 46 is arranged. For the purposes of the explanation let us assume that the light source 46 is a small halogen lamp which approximates to a point light source.

An image of the light source 46 is formed through a lens 48 in the focal point of a small lens 50 of small focal length which thus produces a parallel measurement light beam 52 with small cross-section. The latter then passes into a transparent prism body 56 which is provided with a mirrored deviating surface 58 at the lower end. A measurement light beam which strikes the print product at a small angle of incidence to its surface is obtained in this way. The angle of incidence may be between 2 and 10° in practice.

As can also be seen in FIG. 2, powder particles 60 are arranged on the surface of the print product 12. The surface of the print product itself also has hollows 62 which recess from an ideal surface of the print product 12 denoted by a dashed line 64 and also small elevations 66 which project above this surface.

The measurement head 14 has a housing 68 into whose lower wall a sleeve-shaped lens holder part 70 which carries a lens 72 at its lower end is inserted. A small circular opening 76 is provided in a transverse moulded-on diaphragm body 74 of the holder part 70. The distance between the opening 76 and the principal plane of the lens 72 corresponds to the focal length of this lens or is close to it. An image converter 78 which is carried by a printed circuit board 80 is arranged above the holder part 70. The image converter 78 and the circuit board 80 and the components carried by the latter correspond to the components of a common commercial television camera which perform the same functions.

As can be seen from FIG. 2, the optical axis of the measurement head 14 is vertical to the surface of the print product 12, and if this surface were free from powder particles 60 and ideally flat and smooth, no portions of the measurement light beam 52 would reach the image converter 72. The powder particles 60 located on the surface of the print product, however, scatter portions of the measurement light beam 52 so that the lens 72 generates an image of the powder particles 60 on the image converter 78. The same applies to a lesser degree to the hollows 62 and elevations 66. The more strongly glancing the incidence of the measurement light beam 52 on the surface of the print product 12, the lower the contribution of the hollows 62 and elevations 66 to the image obtained on the image converter 78. With only a very small setting of the measurement light beam 52, this image consists virtually exclusively of the image of the powder particles.

Figure 3:
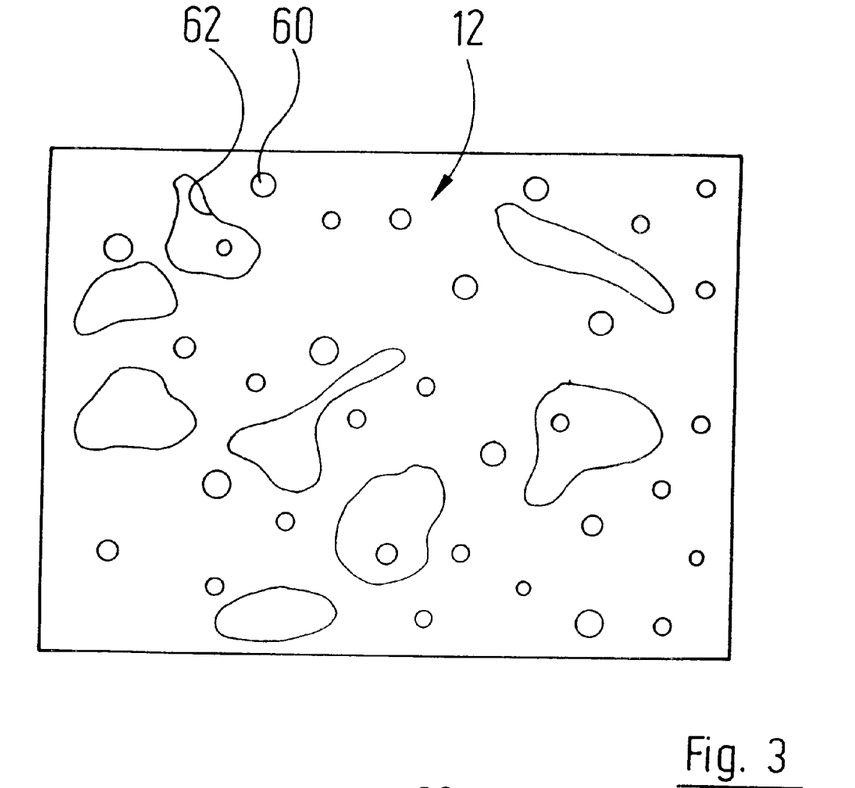
FIG. 3 shows an enlarged view of a part of the surface of the dusted print product as obtained by representation on a monitor of the pixels of an image converter of the measurement head shown in FIG. 2.

FIG. 3 schematically shows an image such as is obtained from the image converter 78 when incidence is not extremely glancing. Powder particles 60 of different size, which are statistically distributed over the image surface, and hollows 62, can be identified. The powder particles 60 appear as light circular discs, the hollows 62 as darker, irregular surfaces.

Figure 4:
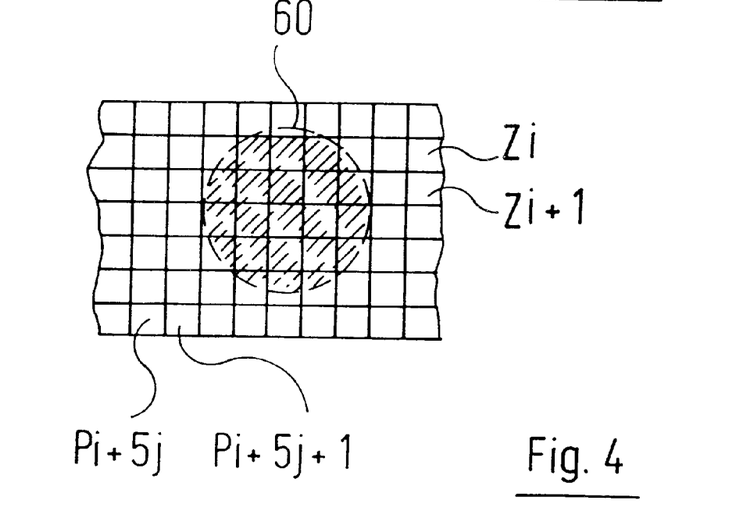
FIG. 4 shows a further enlarged view of a detail of the image of a powder particle generated by the image converter which is used to explain a program section which serves to determine the number and size of powder particles.

As shown in FIG. 4, the image of the image converter 78 is organized in successive lines Z1, Z2, Zi, Zi+1, . . . , which have a sequence of pixels Pi1, Pi2, Pi3, . . . , Pij, Pij+1, . . . in each case.

Figure 5:
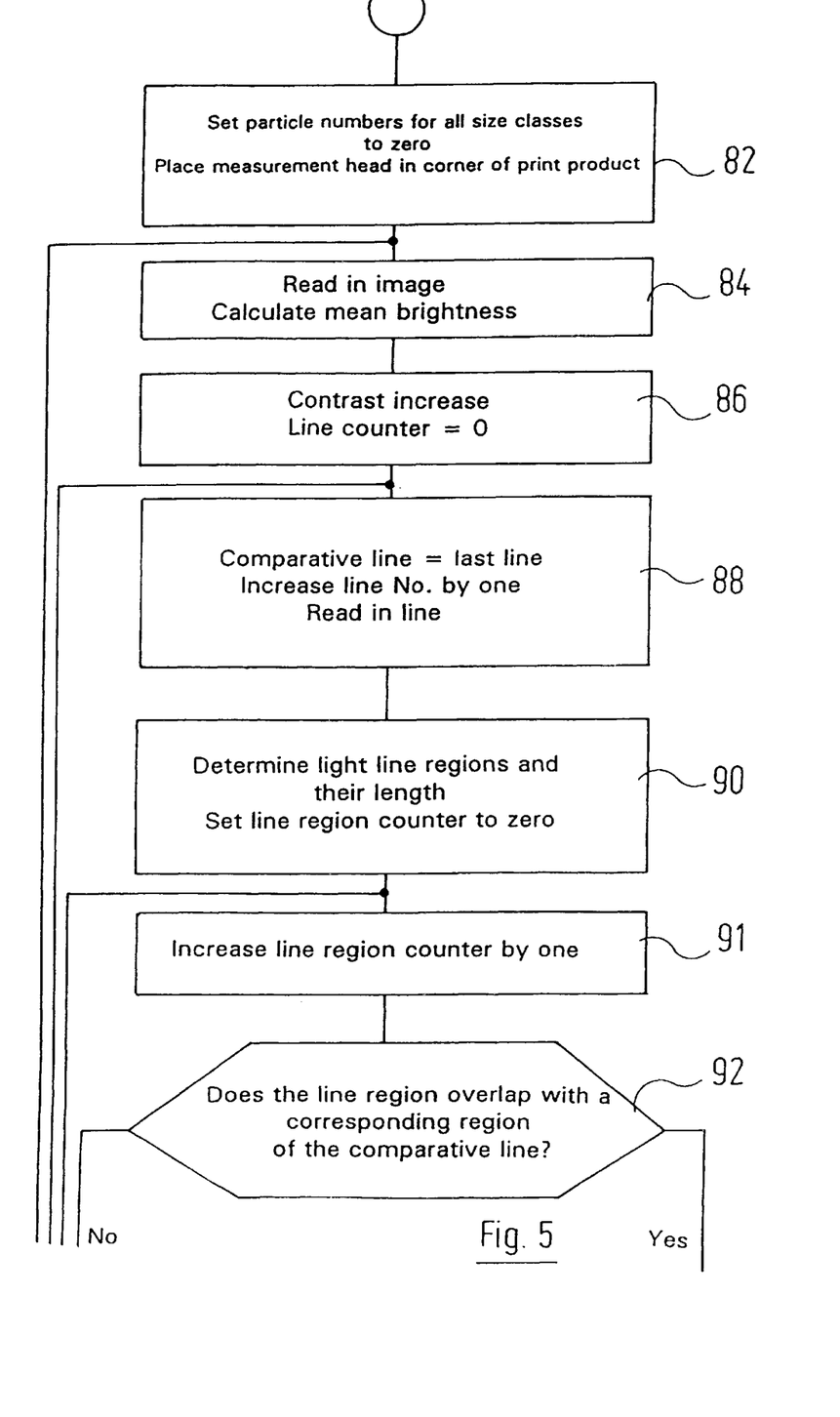
FIG. 5 shows a flow chart in which the most important sections of a program for determining the number and size of powder particles are reproduced.

FIG. 5 shows how the powder density and the size distribution of the powder particles can be determined from the image obtained from the image converter 78. The image is evaluated line-wise.

In an initialization block 82, the particle numbers in the different size classes are initially set to zero and the measurement head 14 moved into a starting position at a sheet corner.

In a further block 84, the particular image of the image converter that is present is read in and the mean image brightness is calculated by adding the brightness values for all pixels and dividing by the total number of pixels.

In a further block 86 a powder image is generated by setting all image pixels whose brightness is greater than the mean value to light, all other image pixels to dark. A line counter is also set to zero.

In a further block 88 the line last evaluated is stored as the comparative line, the line counter increased by one and the next line read in.

In a subsequent program block 90 the light line regions and their length are determined. A line region counter is also set to zero.

In a subsequent program block 91 the line region counter is increased by one.

In a subsequent branch 92, using the comparative line a check is made as to whether a light line region has disappeared or not. If it has, the particle number in the particle class corresponding to the diameter previously determined is increased by one in a program block 94.

If, in the branch 92, it was found that the image region under consideration is a continuation of an image region of the preceding line, in a branch 96 a check is made as to whether the dimension of the corresponding image region has increased or not. If it has, the object diameter is updated in a program block 98.

In a further branch 99 a check is made as to whether the last image region of the line has already been reached or not. If it has not, a return to program block 91 takes place.

In a further branch 100 a check is made as to whether the last line of the image has already been reached or not. If it has not, a return to program block 88 takes place.

In a further branch 102 a check is made as to whether the corner of the print product opposite the starting point has been reached or not. If it has not, in a program block 104 the motors 24 and 32 are controlled in such a way that the measurement head 14 is moved further by one increment on a meandering route which leads from the starting corner of the print product 12 to the opposite corner, or, more generally, from the measurement starting point to the measurement end point.

If, in the branch 102, it is found that the corner of the print product opposite the starting point has already been reached, the mean particle density and mean particle size is calculated in a further program block 106. In a further program block 108 a check is made as to whether particle density and particle size are within a specified window or not. If they are not, an alarm is given, e.g. by displaying an alphanumeric message on the screen of the control and evaluation unit 36.

In modification of the embodiment described above, the slide 27 may also be provided in a stationary manner and the measurement head 14 be moved over the print product only transversely, so that only the transverse powder density profile is measured. It will be understood that in this case the flow chart as shown in FIG. 5 may be simplified correspondingly.

Figure 6:
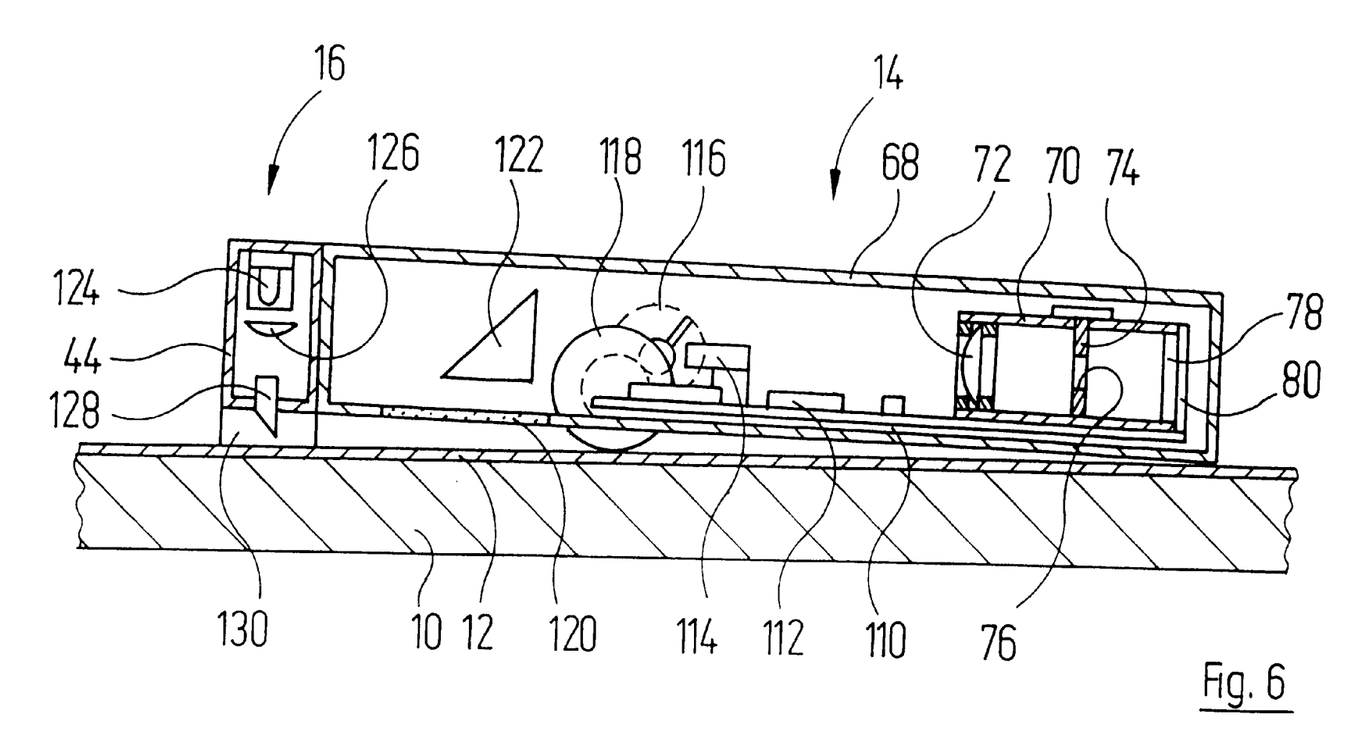
FIG. 6 shows a vertical section through a modified illumination unit and a modified measurement head which are obtained by converting a common commercial hand-held scanner.

FIG. 6 shows a modified measurement head 14, the construction of which extensively corresponds to that of a hand-held scanner, as is used to read texts and graphics into a PC. Parts of the scanner which correspond to parts of the measurement head 14 shown in FIG. 2 from a function point of view are again provided with the same reference numerals.

The holder part 70 is formed as a housing having a rectangular cross-section and on whose rear side the image converter 78 and the circuit board 80 carrying it are directly mounted. The lens mounting is arranged on a further circuit board 110 which is equipped with various electronic components 112 including a fork light barrier 114. This cooperates with a stroboscope disk 116 which is driven by a friction wheel 118 which cooperates with the surface of the print product 12. The image of the surface of the print product 12 is formed via a window 120 provided in the lower wall of the housing 68 and a strip-shaped deviating prism 122 having a triangular cross-section and whose inclined prism side is mirrored.

The illumination unit 16 is mounted on the front face of the housing 68 shown on the left-hand side in FIG. 6. This unit comprises a diode row 124 which comprises a multiplicity of diodes in sequence vertical to the plane of projection of FIG. 6. Via a cylinder lens 126 the image of the diode row 124 is formed on a prism strip 128 which has a mirrored prism surface substantially set at 45° at the lower end.

As can be seen from FIG. 6, two narrow sliding ribs 130 which project downwards over the housing underside are provided at both sides of the housing 44 of the illumination unit 16. A wedge-shaped slit, into whose left-hand end the lower end of the prism strip 128 projects, is produced in this way between the underside of the housing 44 and the underside of the housing 68, which is flush with it, and the upper side of the print product 12. Light is directed in a substantially glancing manner against the surface of the print product 12 through this wedge-shaped slit.

To exclude reflections of marginal rays, the lower surfaces of the housings 44 and 68 are black in color.

The only way in which the measurement head 14 differs from a common commercial hand-held scanner is as follows:

The diode strip therein which serves to illuminate the master is removed and accommodated in the housing 44 of the illumination unit 16 together with the assigned lens strip. Furthermore, the friction wheel provided to drive the stroboscope disk is replaced by a friction wheel which has an enlarged diameter according to the height of the sliding ribs 130. Finally, a hole has been drilled into the upper wall of the housing or holder part 70, through which the diaphragm body 74 is introduced. Its opening 76 is formed as a slit, in view of the fact that the image converter 78 now only comprises one pixel line, the long slit axis lying in the plane of projection and vertical to the axis of the image converter, whereas the short slit axis is vertical to the plane of projection and runs parallel to the converter axis.

In use, the hand-held scanner is simply guided crosswise over a dusting print product under test, and the signals supplied by the line image converter 78 are filed in a read/write memory of the control and evaluation unit 36, which takes place by addressing the individual memory cells as a function of the status of a counter which counts upwards according to the output pulses of the fork light barrier 114. An image of a region of the powder layer running crosswise over the print product is thus obtained in the read/write memory. This image can be evaluated in a similar way to that described above.

It will be understood that the measurement apparatus shown in FIG. 6 may equally also be used to measure the surface roughness of a print support to be printed, as described in detail above with reference to the measurement apparatus of FIG. 1.

As a modification of the embodiments explained above, the angle at which the measurement light beam strikes the surface of the print product may also be rendered adjustable, e.g. by tilting the lens 50 or the lens strip 126 or deflecting them in the lateral direction. In this case a somewhat enlarged angle between measurement light beam and surface of the print product may be used in the roughness measurement whereas light incidence that is as glancing as possible is again employed for determining the powder density.

What is claimed is:

1. An apparatus for determining the powder density on a dusted print product (12) with an illumination unit (16), which generates a measurement light beam (52) directed in an inclined manner towards the surface of the print product (12), with a measurement head (14) which has: an optics (72), whose axis is set at an angle to the surface of the print product (12) which differs in value from the setting angle of the measurement light beam (52), and an image converter (78), which is arranged in the focal plane of the optics (72), and with an evaluation unit (36) for determining the number of objects (60, 62, 66) whose images are formed on the image converter (78) and which are located on the surface of the print product (12), wherein a diaphragm body (74) is arranged in the vicinity of the focal point of the optics (72) on the image side.

2. An apparatus as claimed in claim 1, wherein the image converter (78) is an image converter comprising a two-dimensional pixel arrangement and the diaphragm body (74) has a circular opening (76).

3. An apparatus as claimed in claim 1, wherein the image converter (78) is an image converter comprising a one-dimensional pixel arrangement and the diaphragm body (74) has a slit-shaped opening, the slit axis running vertical to the axis of the pixel line of the image converter (78).

4. An apparatus as claimed in claim 1, wherein it comprises at least one servo-drive (24, 32) for moving the measurement head (14) and the illumination unit (16) over the print product (12).

5. An apparatus as claimed in claim 4, wherein it comprises a control unit (36) working on the servo-drive (24, 32) which controls the servo-drive (24,32) in such a way that the measurement head (14) and the illumination unit (16) are moved intermittently by stretches corresponding to the size of an image field.

6. An apparatus as claimed in claim 1, wherein the measurement head (14) is formed by a substantially common commercial scanner which is additionally provided with the diaphragm body (74) between its optics (72) and the image converter (78) and in which the optics (72) and/or the illumination unit (16) have been displaced in such a way that their axes do not correspond to the reflection condition.

7. A measurement apparatus as claimed in claim 1, wherein the illumination unit (16) generates a measurement light beam (52) inclined at a small angle of approx. 2° to approx. 10° to the surface of the print product (12) and striking the print product at grazing incidence and the axis of the optics (72) is substantially vertical to the surface of the print product (12).

8. An apparatus as claimed in claim 7, wherein the illumination unit (16) comprises a deflecting mirror (58) adjacent to the surface of the print product (12).

9. An apparatus as claimed in claim 1, wherein the housing surfaces of the measurement head (14) and of the illumination unit (16) facing the surface of the print product (12) are formed as surfaces absorbing the measurement light.

10. An apparatus as claimed in claim 6, wherein the illumination unit (16) has an additional housing (44) placed on the housing (68) of the scanner.

11. An apparatus as claimed in claim 10, wherein the scanner is a hand-held scanner and the additional housing (44) has sliding ribs (130) hanging downwards over the underside of the scanner housing.

12. An apparatus as claimed in claim 1, wherein the evaluation unit (36) generates an image of the powder particles (60) from the image read out by the image converter (78) by calculating the mean brightness of all pixels for the entire image or an image line and using for the powder image those image pixels in which the brightness is greater than the mean brightness.

13. An apparatus as claimed in claim 1, wherein the evaluation unit (36) generates an image of surface roughnesses from the image read out by the image converter (78) by calculating the mean brightness of all pixels for the entire image or an image line and using for the roughnesses image those image pixels in which the brightness is less than the mean brightness.

14. An apparatus as claimed in claim 13, wherein the evaluation unit (36) exchanges the dark regions and the light regions of the roughness image.

15. An apparatus as claimed in claim 12, wherein the evaluation unit (36) determines light image regions and dark image regions and their length for every line of the image.

16. An apparatus as claimed in claim 15, wherein the evaluation unit (36) determines whether the light image regions of successive image lines overlap and increases a particle counter by one in each case, if an image region was determined in the preceding image line which is no longer present in the current image line.

17. An apparatus as claimed in claim 15, wherein for each image region determined the evaluation unit (36) equates a region size variable to the image region length determined in the image line present when the image region length is greater than the region size variable.

18. An apparatus as claimed in claim 11, wherein the evaluation unit (36) generates an alarm signal (108) if the powder density in a region of the surface of the print product (12) is below a specified minimum value.

19. An apparatus as claimed in claim 11, wherein the evaluation unit (36) generates an alarm signal (108) if the powder density in a region of the surface of the print product (12) is above a specified maximum value.

20. An apparatus as claimed in claim 1, wherein the evaluation unit (36) has a fixed-value memory in which working values for particle size and powder density are filed for different roughness values of print supports and displays a set of these working values according to the roughness measured in each case.

21. An apparatus as claimed in claim 1, wherein it comprises a device for adjusting the angle of incidence of the measurement light beam.

22. An apparatus as claimed in claim 1, wherein the evaluation unit also serves for determination of the size of the objects (60, 622, 66).

23. An apparatus for determining the powder density on a dusted print product (12) with an illumination unit (16), which generates a measurement light beam (52) directed in an inclined manner towards the surface of the print product (12), with a measurement head (14) which has: an optics (72), whose axis is set at an angle to the surface of the print product (12) which differs in value from the setting angle of the measurement light beam (52), and an image converter (78), which is arranged in the focal plane of the optics (72), and with an evaluation unit (36) for determining the number of objects (60, 62, 66) whose images are formed on the image converter (78) and which are located on the surface of the print product (12), and at least one servo-drive (24, 32) for moving the measurement head (14) and the illumination unit (16) over the print product (12), wherein a diaphragm body (74) is arranged in the vicinity of the focal point of the optics (72) on the image side.

24. An apparatus for determining the powder density on a dusted print product (12) with an illumination unit (16), which generates a measurement light beam (52) directed in an inclined manner towards the surface of the print product (12), with a measurement head (14) which has: an optics (72), whose axis is set at an angle to the surface of the print product (12) which differs in value from the setting angle of the measurement light beam (52), and an image converter (78), which is arranged in the focal plane of the optics (72), and with an evaluation unit (36) for determining the number of objects (60, 62, 66) whose images are formed on the image converter (78) and which are located on the surface of the print product (12), wherein a diaphragm body (74) is arranged in the vicinity of the focal point of the optics (72) on the image side, and the measurement head (14) is formed by a substantially common commercial scanner which is additionally provided with the diaphragm body (74) between its optics (72) and the image converter (78) and in which the optics (72) or the illumination unit (16) have been displaced in such a way that their axes do not correspond to the reflection condition.

25. An apparatus for determinint the powder density on a dusted print product (12) with an illumination unit (16), which generates a measurement light beam (52) directed in an inclined manner towards the surface of the print product (12), with a measurement head (14) which has: an optics (72), whose axis is set at an angle to the surface of the print product (12) which differs in value from the setting angle of the measurement light beam (52), and an image converter (78), which is arranged in the focal plane of the optics (72), and with an evaluation unit (36) for determining the number of objects (60, 62, 66) whose images are formed on the image converter (78) and which are located on the surface of the print product (12), wherein a diaphragm body (74) is arranged in the vicinity of the focal point of the optics (72) on the image side, and the evaluation unit (36) generates an image of the powder particles (60) from the image read out by the image or an image line and using for the powder image those image pixels in which the brightness is greater than the mean brightness.

26. An apparatus as claimed in claim 1, wherein the diaphragm body (74) is arranged at the focal point.

* * * * *